United States Patent [19]
Förster

[11] Patent Number: 5,820,371
[45] Date of Patent: Oct. 13, 1998

[54] DEVICE FOR TOOTH-POSTITION CORRECTION

[75] Inventor: Rolf Förster, Pforzheim, Germany

[73] Assignee: Bernhard Forster GmbH, Pforzheim, Germany

[21] Appl. No.: 809,948

[22] PCT Filed: Sep. 25, 1995

[86] PCT No.: PCT/EP95/03783

§ 371 Date: May 5, 1997

§ 102(e) Date: May 5, 1997

[87] PCT Pub. No.: WO96/09015

PCT Pub. Date: Mar. 28, 1996

[30] Foreign Application Priority Data

Sep. 24, 1994 [DE] Germany .......... 44 34 209.8

[51] Int. Cl.$^6$ .................... A61K 3/00
[52] U.S. Cl. ................................. 433/9
[58] Field of Search ................... 433/8, 9, 24

[56] References Cited

U.S. PATENT DOCUMENTS

| | | | |
|---|---|---|---|
| 4,661,059 | 4/1987 | Kanno | 433/9 |
| 4,838,786 | 6/1989 | Reber et al. | 433/9 |
| 5,297,854 | 3/1994 | Schmitt | 433/9 X |
| 5,380,196 | 1/1995 | Kelly et al. | 433/8 |
| 5,441,408 | 8/1995 | Moschik | 433/9 X |
| 5,622,494 | 4/1997 | Andreiko et al. | 433/9 |

*Primary Examiner*—Nicholas D. Lucchesi
*Attorney, Agent, or Firm*—Dvorak & Orum

[57] ABSTRACT

A device for tooth-position correction includes a bracket or buccal tube formed from a plastic material by the injection-molding process, having a pad with a concave underside for connection onto the front face of a tooth, and an upper face from which extends an integrally formed mounting and guide element for receiving an arch wire. The underside of the pad is provided with projections having undercuts formed by bars placed on the underside during the injection-molding process.

17 Claims, 3 Drawing Sheets

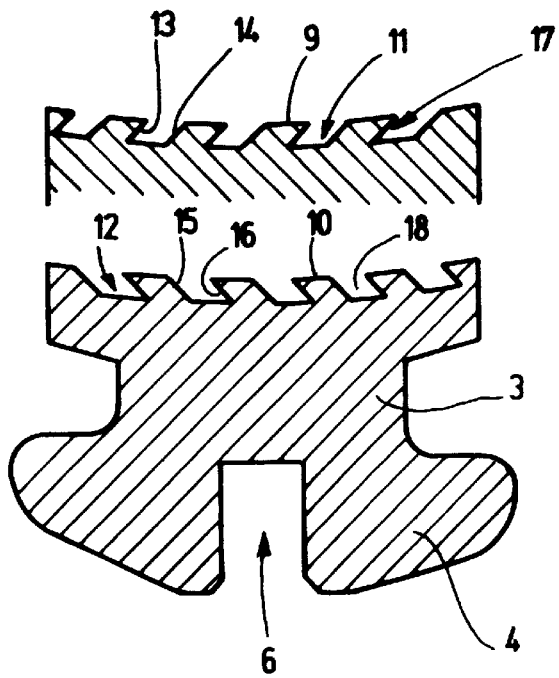
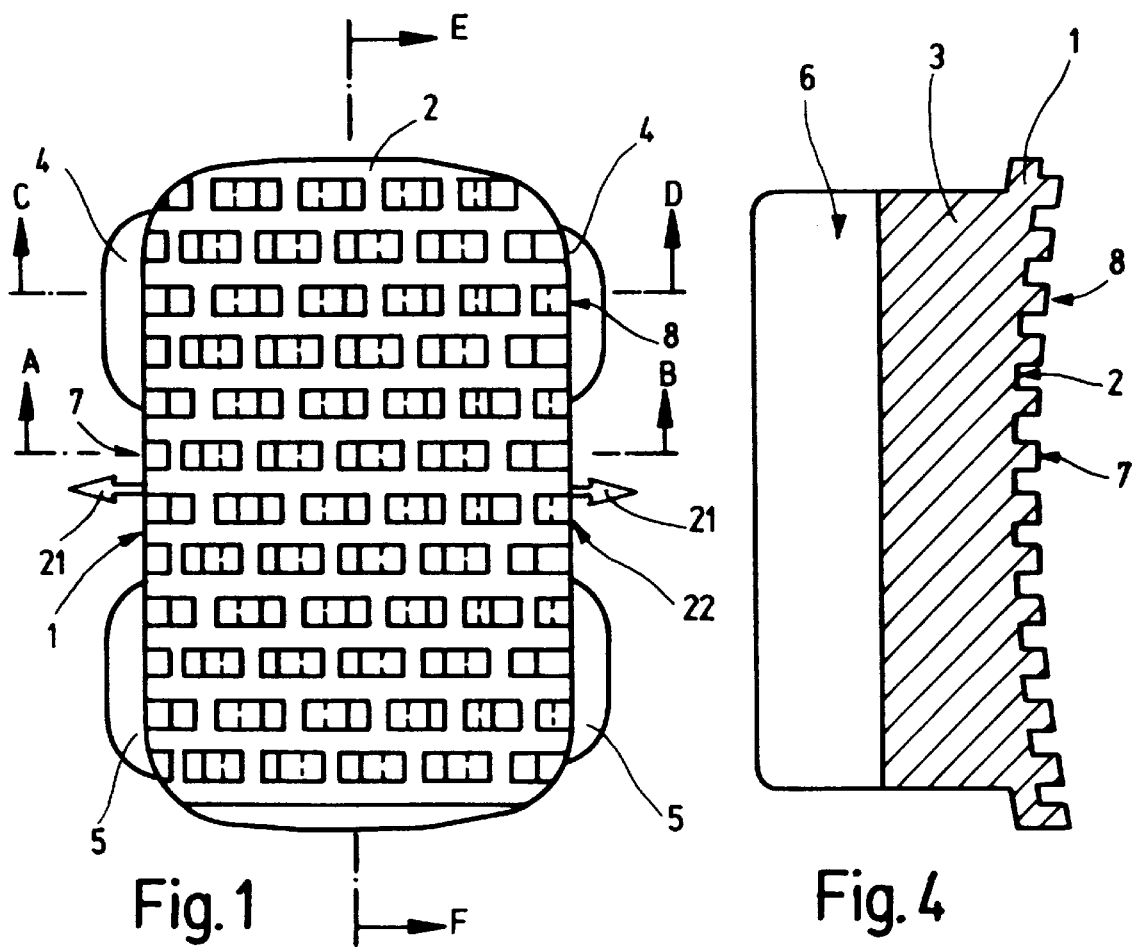

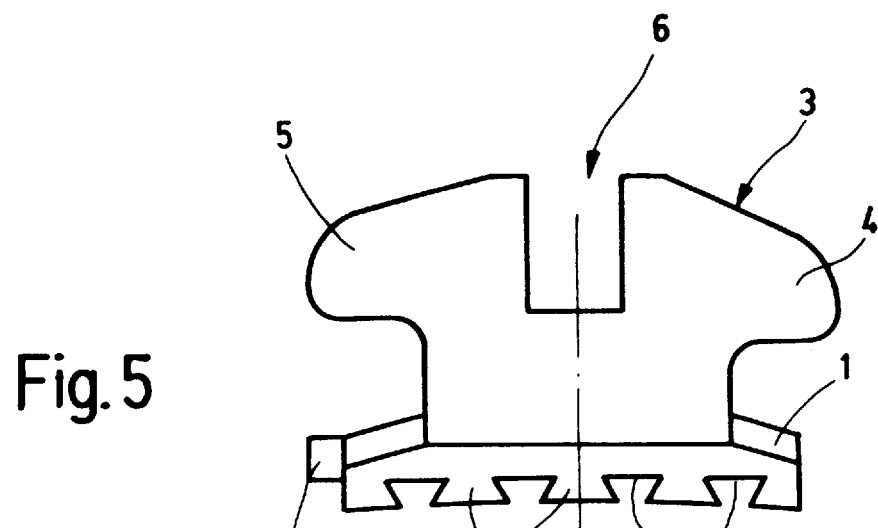
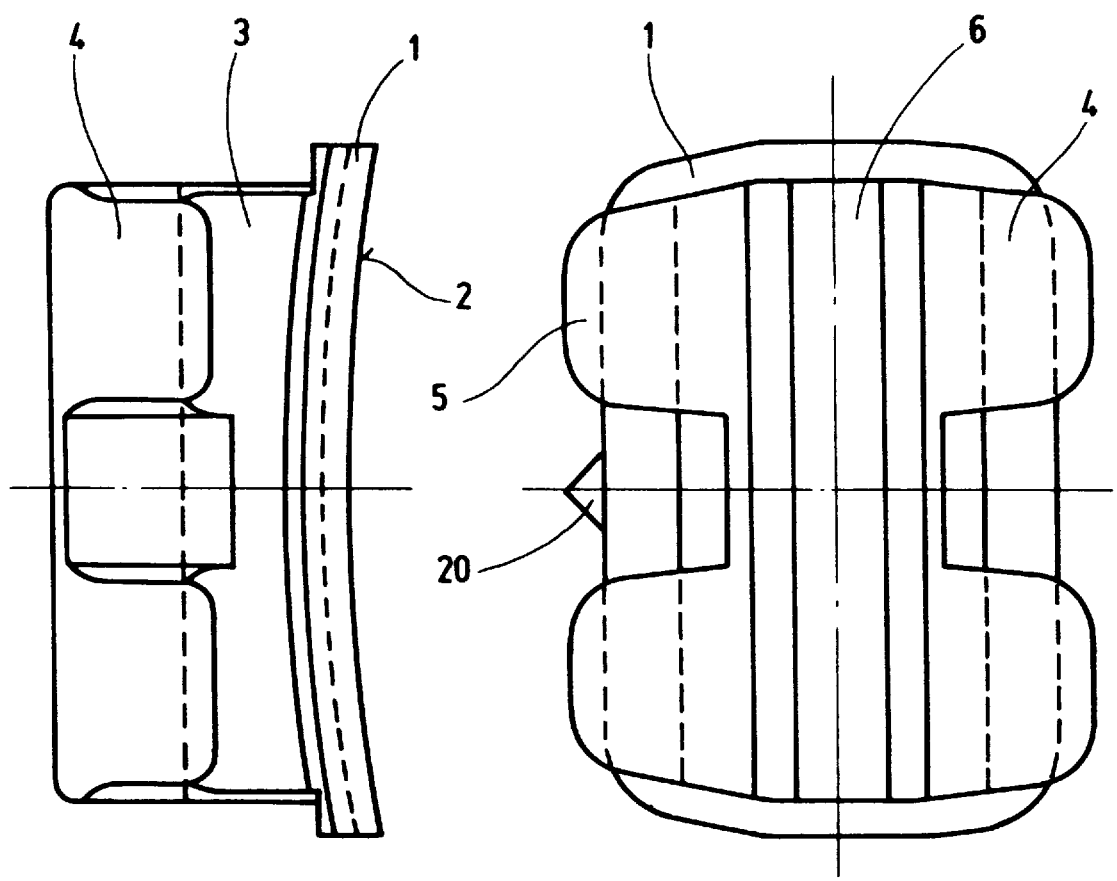

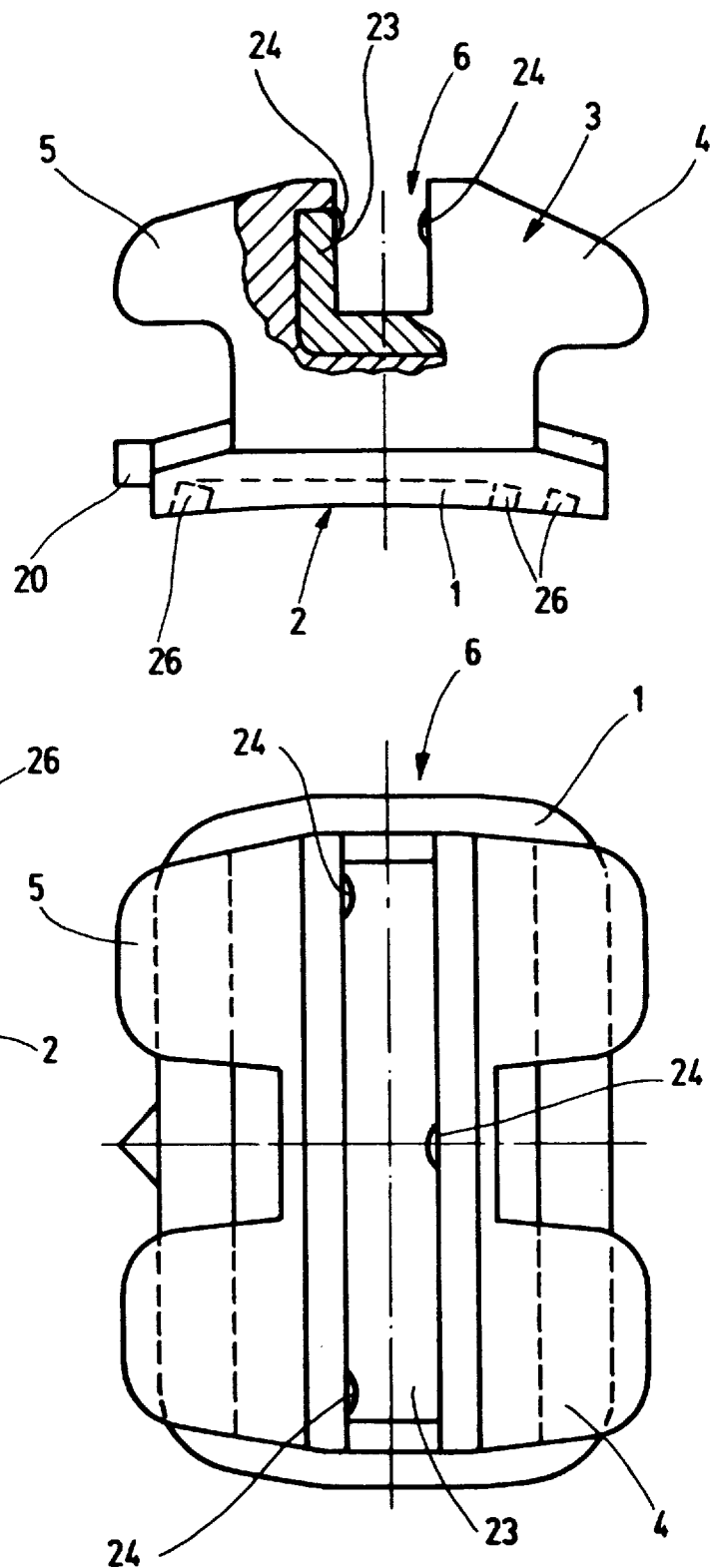

DEVICE FOR TOOTH-POSTITION CORRECTION

The present invention pertaining to a device for receiving and guiding arch wires and for transferring onto the tooth the forces resulting from their mechanical tension. They comprise for this purpose a pad with a concave underside, intended for being pasted onto the front face of a tooth, and a mounting and guide element for the wire that projects from the upper face of the pad. The underside of the pad is pasted onto the front surface of the tooth. In order to permit the forces exerted by the arch wire to be transferred onto the tooth, it is necessary that the adhesive bond be strong and durable. With the known tooth-position correction devices, which in most of the cases are made from stainless steel, the underside of the pad is provided for this purpose with a wire mesh which has the effect that in addition to the adhesive bond a mechanical interlock is obtained between the pad and the adhesive. In U.S. Pat. No. 5,267,854 there is described a metal bracket, which is produced by powder metallurgy processes, where blanks are first molded with the aid of a multiple mold, then removed from the mold and stabilized by sintering. The brackets so produced are provided with rodshaped projections on the underside of the pad, which slightly taper toward their outer ends in order to enable them to be removed from the mold. After the sintering process, the projections are then compressed by the action of a press die to give them a mushroom-like shape. This mushroom-like shape allows them to interlock with the adhesive used for pasting them onto the teeth. The production of these known brackets is relatively expensive, and this the more as the press die used for shaping the projections requires a counter-die adapted in shape to match the contour of the mounting and guide element of the bracket.

As an additional aspect, stainless steel brackets contain nickel. In view of reports regarding contact allergies that are said to be caused by nickel, efforts have been made to produce tooth-position correction devices from materials that do not contain any nickel. At present, titanium is the only known metallic material that can be used for medical purposes without producing any allergic reactions. But titanium is relatively difficult to work.

There have also been known brackets made from ceramics which do not produce any allergic reactions, but which are by their nature relatively brittle so that they tend to break easily.

Further, brackets have been known to be made from thermoplastic synthetic materials, i.e. from clear polycarbonate. They were originally developed because they are less noticeable in the mouth than metallic brackets. The adhesive used for pasting the brackets onto the teeth have the tendency to bite polycarbonate so that the adhesive and the pad are firmly bonded one to the other, by chemical means, whereby any mechanical interlock between the pad and the adhesive is rendered superfluous. Brackets made from polycarbonate may, therefore, have a flat underside which is favorable in terms of the removal from the mold after the molding process. Being free from nickel, brackets made from polycarbonate are substituted to an increasing extent for the previously used stainless steel brackets. Unfortunately, however, brackets made from polycarbonate lack in mechanical strength and, thus, in durability and inherent stability.

Plastic brackets known from U.S. Pat. No. 4,604,057 are provided on the underside of the pad with inclined recesses which are delimited by parallel surfaces and which are formed as part of the injection-molding process. Plastic brackets known from U.S. Pat. No. 5,254,002, are provided with a slot, which is reinforced by a metallic insert and is intended to absorb the tension forces produced by an arch wire.

Polyarylether ketones (PAEK) have vary favorable properties in terms of the invention. Non-reinforced PAEK already offers a well-balanced combination of high rigidity and strength, with good toughness, high inherent thermal stability and good kinetic friction properties. As regards its strength and rigidity, PAEK is superior to most technical plastic materials. Still higher strength and rigidity values can be achieved if the PAEK is reinforced, in particular with glass or carbon fibers. In addition, PAEK has excellent resistance to chemicals, although this resistance is connected with one disadvantage in that it has the result that the non-toxic and biocompatible adhesives, that can be used for applications in the mouth, are not capable of biting PAEK. It is, therefore, not possible to use brackets that differ from polycarbonate brackets only in that PAEK is substituted for polycarbonate, as such brackets cannot be pasted to the teeth with the required bonding strength. Thus, it is an object of the present invention to provide nickelfree brackets that can be produced at low cost, have sufficient toughness and strength to withstand the tension forces exerted by the arch wires for the whole duration of a tooth-position correction treatment, and that can be pasted onto the teeth solidly and durably, with the aid of the adhesives normally used and proven for dental purposes.

This object is achieved by devices for correcting the tooth position having the features specified in claim 1. Advantageous further developments of the invention are specified in the dependent claims.

SUMMARY OF THE INVENTION

The invention proposes to produce brackets and buccal tubes from plastic materials by injection molding, and to form on the underside of the pads, by the same injection-molding process, projections or recesses of undercut shape. Consequently is now for the first time possible, with correction devices made from plastic materials, to provided a mechanical interlock between the underside of the pad and the adhesive used for bonding the pad to the tooth. This provides the necessary preconditions that allow plastic materials of high strength and toughness, but of extraordinary chemical resistance, such as PAEK, to be used for purposes of the invention and that permit brackets and buccal tubes made from such materials to be bonded to the teeth. The relevant prior art does not contain any indication that would suggest to shape the underside of the pads of brackets and buccal tubes in the manner claimed by the present invention. In the case of the known brackets made from polycarbonate the underside of the pads is either smooth or rough or profiled, but is never provided with undercuts. To roughen the underside of the pads, or to provide them with a waffle pattern would only increase the surface of the pad, whereas the circumstance that the adhesive, being chemically resistant, does not interlace with the plastic material of the pad would not be changed in any way. To provide the underside of the pads with a mesh of the kind used with stainless-steel brackets, also does not lead to the desired success, as the high temperatures, at which the mesh would have to be bonded to the underside of the pad (over 250° Celsius) would cause the mesh to disappear, leaving at best a certain undulation on the back of the pad. A similar result would be achieved by transferring-with all reservations-the method described by U.S. Pat. No. 5,267,854 for sintered metal brackets to the production of plastic brackets by the injection-molding process. Rod-shaped, slightly conical projections on the underside of the pad could of course be produced by injection-molding processes and could be removed from the mold, but compressing them with the aid of a press die to give them a mushroom-like shape, in a manner analogous to that described by U.S. Pat. No. 5,267, 854, would in principle not be feasible with a cold die, but would require a hot die which, however, would cause the projections, which are only a few tenths of a millimeter long, to melt down practically immediately so that at best a somewhat undulated underside of the pad would be obtained which would not be capable of interlocking mechanically with the adhesive.

Surprisingly, it has been found that projections with such tiny dimensions, and recesses of the kind required on the underside of the pad can be injection-molded, in spite of their tiny shape, in such a way that when leaving the injection mold they already have an undercut capable of producing an effective mechanical interlock with an adhesive of the kind normally used in dental technology. The invention therefore provides a number of advantages all at the same time:

The tooth-position correction devices according to the invention, namely brackets and buccal tubes, can be produced in a single operation, by injection-molding them from a plastic material. In addition, the underside of the pad does not have to be subjected to any pretreatment for the purpose of allowing the parts to be connected with the teeth by an adhesive.

Even plastic materials that have a chemical resistance as extraordinary as PAEK can be pasted onto the teeth solidly and durably with the aid of the adhesives normally used in dental technology, so that this proven bonding technique can now be used even for plastic materials having the high strength and toughness of PAEK.

The fact that injection molding is the only process employed for the production, the latter can be carried out at very low cost.

PAEK naturally has a light grayish/beige color which resembles the natural color of teeth rather closely and has a lower tendency to produce reflections than that of polycarbonate, such that PAEK elements will hardly be noticed in the mouth.

If desired, the color of PAEK can be lightened by the addition of light color pigments that are added to the PAEK granules prior to the injection-molding process or during production of the granules. A suitable lightener is TiO powder (titanium white).

The projections, which conveniently do not project by more than 0.5 mm, preferably by not more than 0.3 mm, and the recesses which conveniently are not deeper than 0.5 mm, preferably not deeper than 0.3 mm, are conveniently arranged in straight, mutually parallel rows in order to facilitate the use of a system of miniaturized bars, with the aid of which the undercuts are to be formed in the injection mold by which the parts are to be molded. Where the underside of the pad is not curved, or only slightly curved in the direction of the rows, T-shaped, hook-shaped, and especially L-shaped projections can be molded with bars extending parallel to the underside of the pad. Undercuts formed by bars that are released vertically or at an angle to the vertical, related to the underside of the pad, are particularly well-suited for easily flowing adhesives, especially two-compound adhesives, because these tend to flow more easily behind undercuts formed in this way.

Projections with trapezoidal or rhomb-shaped cross-section, in vertical direction to the underside of the pad, and recesses can be formed with the aid of bars extending at an angle to the pad surface, in which case undercuts can be produced regardless of the curvature of the pad surface. It is particularly preferred in this connection to give the projections a rhomb-shaped cross-section, in vertical direction to the underside of the pad; this allows the underside of the pad to be packed very tightly with undercut projections, which in turn results in excellent interlocking with the adhesive. An especially effective interlock is achieved when the undercuts are oriented in different directions. It is, therefore, preferred to make all the projections in one row identical with the other and mirror-images with the projections of the neighboring row or the two neighboring rows. Building the arrangement from identical or mirror-image projections simplifies the structure of the injection mold, while at the same time the mirrored orientation of the undercuts results in especially efficient interlocking with the adhesive.

According to a further development of the invention, the injection-molded parts are preferably provided with prolongations that extend in vertical direction relative to the occlusion plane and that are connected with the mounting and guide element through a rupture joint. These prolongations, which can easily be molded together with the part itself, can be used as installation aid to facilitate the alignment of the part on the tooth axis, by indicating the theoretical line along which the tooth axis should extend relative to the bracket or buccal tube. Once the part is properly aligned on the tooth and the adhesive has cured, the projections can be simply torn off or broken away or cut off. Compared with conventional installation aids, imprinted on the part, these prolongations have the advantage that they can be removed without presenting the risk of being wiped off prematurely. Compared with conventional installation aids, which are pressed into slots provided in the bracket, they present the advantage that there is no separate part that must be pressed into a slot during installation of the bracket.

Brackets according to the invention adhere to the teeth so strongly that the tension forces applied through arch wires may be high enough to cause even plastic materials with the strength of PAEK to start creeping. A further development of the invention, therefore, proposes to reinforce the slot, intended to receive the wire arch, by an insert made from ceramics or metal, which could of course be fixed by bonding, but which is preferably embedded during the molding process, most conveniently in such a way that its outer edges are covered by the plastic material so that a positive connection is obtained. In addition, the insert will then not attract attention, optically.

If no such inserts are provided, the upper portion of the slot may advantageously be provided with knobs or similar projections behind which the arch wire can engage.

The invention can be transferred to the production of tooth-position correction devices made from other injection-moldable materials, instead of a plastic material. This group of materials includes materials that can be processed by powder metallurgy processes, such as aluminium oxide.

DETAILED DESCRIPTION OF THE DRAWINGS

Some exemplary embodiments of the invention are illustrated in the attached drawings in which:

FIG. 1 shows a view of the underside of a bracket;

FIG. 2 shows a sectional view of the bracket along line A—A of FIG. 1;

FIG. 3 shows a sectional view of the bracket along line B—B of FIG. 1;

FIG. 4 shows a sectional view of the bracket along line C—C of FIG. 1;

FIG. 5 shows a side view of another bracket, with dovetail-shaped projections;

FIG. 6 shows a top view of the bracket according to FIG. 5;

FIG. 7 shows another side view of the bracket according to FIG. 5; and

FIGS. 8 to 10 show three views, according to FIGS. 5–7, of another bracket with recesses in the underside of the pad and with reinforced slot.

DETAILED DESCRIPTION OF THE PREFERRED EMBODIMENT

The bracket shown in FIGS. 1 to 4 comprises a pad 1 with concave underside 2. The upper face of the pad 1 carries a two-winged mounting and guide element 3 with a slot 6, passing through the two wings 4 and 5, being intended for receiving an arch wire that is to be tensioned.

The underside 2 of the pad 1 is provided with two mutually parallel rows of projections, two of them, namely row 7 and row 8 in FIG. 1, being shown in cross-section by way of example in FIGS. 2 and 3. Except for the projections adjacent the edge, the projections of the different rows are identical one with the other, namely rhomb-shaped (see FIGS. 2 and 3), the projections 9 in row 7 being provided in mirrored orientation with respect to the projections 10 in row 8. Similarly, the projections of each row are provided in mirrored arrangement relative to the projections in the neighboring rows.

More important than the or mirror-image identical configuration of the projections 9 is 10 is, however, the identical or mirror-image configuration of the gaps 11 and 12, respectively, between the two projections 9 and 10, respectively, in each row. Due to the rhomb-shaped configuration of the projections 9 and 10, the gaps 11 and 12 have a corresponding complementary shape. The marginal areas 13 and 14, and 15 and 16, respectively, of the projections that delimit the gaps 11 and 12, respectively, should extend in parallel relationship relative one to the other, or should widen slightly toward the outside, to facilitate their removal from the mold. This gives the gaps 11 and 12 a predetermined orientation at an angle to the underside 2 of the pad, and these two orientations, which alternate between one row and the next, can be used as orientation for introducing the bars into the cavity of the injection mold in order to keep the gaps 11 and 12 between the projections 9 and 10 free from injection compound during molding of the bracket. Due to the inclined orientation the gaps, and hence the bars; the projections then exhibit on their one side an undercut 17 and 18, respectively, which ensures effective interlocking with the adhesive when the bracket is pasted onto a tooth.

Midway between the two wings 4 and 5, there are provided on the pad 1 two prolongations 20 and 21 that point in opposite directions and that are connected with the pad via a rupture joint 22. The prolongations 20 and 21 serve as installation marks and can be broken away once the bracket is correctly aligned on the tooth axis.

In the other embodiments a like reference numerals have been used to designate those elements that correspond to the respective elements in the first example.

The bracket depicted in FIGS. 5 to 7 differs from that depicted in FIGS. 1 to 4 especially in that to achieve mechanical interlocking with an adhesive, the underside of the pad is provided with straight, dovetail-shaped projections 9, which may be produced with the aid of dovetail-shaped bars in the injection mold, which then leave correspondingly shaped grooves 25 on the underside of the pad 1.

The bracket depicted in FIGS. 8 to 10 comprises blind holes 26 in the underside of pad 1, formed with the aid of injection-mold bars that are oriented at an angle relative to the underside of the pad 1. Not visible in the side views of FIGS. 8 and 10, they are indicated in these Figures only by broken lines. Further, the bracket comprises an insert 23, made from titanium or a ceramics material, as reinforcement of the slot 6. The outer edges of the embedded insert 23 are covered by the plastic material. The insert comprises inwardly directed projections 24 behind which an arch wire can be locked in slot 6. Projections 24 of this kind can be embedded in the bracket during the molding process in the case of the previously described examples.

It is understood that the invention can be applied with advantage for the production not only of brackets, but of any kind of parts used for tooth-.position correction purposes, that are adhered to the tooth in a similar way with the aid of a pad.

I claim:

1. A device for tooth-position correction, made by an injection-molding process from one of a plastic material and other injection-moldable material, comprising:

a pad having a concave underside for attachment onto the front face of a tooth, and an upper face from which extends a mounting and guide element for receiving an arch wire therein, which said mounting and guide element is integrally molded with the pad, the underside of the pad provided with a plurality of parallel rows containing seriatim arranged projections, said projections defined by undercuts formed therein, wherein the projections in an individual row have said undercuts facing a same direction and wherein all said projections in an adjacent row have said undercuts facing an opposite direction, said rows of same facing undercuts alternating to said rows of opposite facing undercuts.

2. The device according to claim 1, wherein the projections are of a cross-sectional shape selected from the group consisting of a hook-shape, an L-shape, rhomboid shape, and a trapezoidal shape.

3. The device according to claim 1, wherein the projections are arranged in straight, mutually parallel rows.

4. The device according to claim 3, wherein the projections are mirror images with the projections of two neighboring rows on either side of said one row.

5. The device according to claim 1, wherein the projections of adjacent rows are mirror images with the other.

6. The device according to claim 1, wherein the mounting and guide element has a slot for receiving the arch wire, which said slot is lined with an insert made from one of a metal and a ceramics material.

7. The device according to claim 6, wherein the insert has outer edges and said outer edges are covered by plastic.

8. The device according to claim 1, wherein the mounting and guide element has a slot for receiving the arch wire, which said slot includes an upper area and integrally molded projections formed in its upper area.

9. The device according to claim 1, wherein the plastic material is selected from the group consisting of a polyarylether ketone, an acetal resin, and a polyoximethylene homopolymer.

10. The device according to claim 9, wherein the plastic material contains a white pigment such as TiO powder.

11. The device according to claim 1, wherein one of the mounting and guide element and pad are provided with a pair of opposed prolongations attached through a rupture joint, said prolongations extending in a direction normal to the slot.

12. The device according to claim 1, wherein the undercuts are formed during the molding process with the aid of a plurality of bars, the bars extending in parallel fashion with respect to each other on the underside of the pad.

13. A device for tooth-position correction, made by an injection-molding process from one of a plastic material and other injection-moldable material, comprising:

a pad having a concave underside for attachment onto the front face of a tooth, and an upper face from which extends a mounting and guide element for receiving an arch wire therein, which said mounting and guide element is integrally molded with the pad, the underside of the pad provided with a plurality of parallel rows of recesses, each of said recesses in the form of a blind bore, such that all recesses in an individual row have said recesses facing a same direction and wherein all said recesses in an adjacent row have said recesses facing an opposite direction, said rows of same facing recesses alternating to said rows of opposite facing recesses.

14. The device according to claim 13, wherein the recesses in one row are mirror images to the recesses in the other row.

15. The device according to claim 13, wherein the recesses in one row are mirror images with the recesses in two adjacent rows on each side of said one row.

16. A device for tooth-position correction, made by an injection-molding process from one of a plastic material and other injection-moldable material, comprising:

a pad having a concave underside for attachment onto the front face of a tooth, and an upper face from which extends a mounting and guide element for receiving an arch wire therein, which said mounting and guide element is integrally molded with the pad, the underside of the pad provided with a plurality of parallel rows containing seriatim arranged projections, said projections defined by undercuts formed therein by the injection-molding process, wherein the projections have a cross-sectional shape such that said projections are separated by parallel grooves in a first direction and by inclined slots in a second direction, said inclined slots extending between said parallel grooves wherein said inclined slots in a first row all face one direction, while said inclined slots in a second row all face an oposite direction, said underside configured with alternating first and second rows.

17. The device according to claim 16 wherein said inclined slots are defined by angles of inclination, said angles of inclination in said first row all inclined to the right and the angles of inclination in said second row all inclined to the left.

* * * * *